(12) United States Patent
Powell et al.

(10) Patent No.: US 11,504,172 B2
(45) Date of Patent: Nov. 22, 2022

(54) VARIABLE STIFFNESS HAMMERTOE K-WIRE AND METHODS FOR USE

(71) Applicant: Arthrex, Inc., Naples, FL (US)

(72) Inventors: Chris Powell, Naples, FL (US); Matthew Fonte, Concord, MA (US); Robert Devaney, Auburndale, MA (US); Paul Fein, Maynard, MA (US); Vincent Weaver, Sudbury, MA (US)

(73) Assignee: Arthrex, Inc., Naples, FL (US)

( * ) Notice: Subject to any disclaimer, the term of this patent is extended or adjusted under 35 U.S.C. 154(b) by 232 days.

(21) Appl. No.: 16/671,803

(22) Filed: Nov. 1, 2019

(65) Prior Publication Data

US 2020/0138490 A1 May 7, 2020

Related U.S. Application Data

(60) Provisional application No. 62/754,023, filed on Nov. 1, 2018.

(51) Int. Cl.
*A61B 17/72* (2006.01)
*A61B 17/84* (2006.01)
*A61F 2/42* (2006.01)
*A61B 17/00* (2006.01)

(52) U.S. Cl.
CPC ........ *A61B 17/7291* (2013.01); *A61F 2/4225* (2013.01); *A61B 2017/00862* (2013.01); *A61B 2017/00867* (2013.01); *A61B 2017/00946* (2013.01); *A61F 2002/4228* (2013.01)

(58) Field of Classification Search
CPC ............... A61B 17/7291; A61F 2/4225; A61F 2002/4228
See application file for complete search history.

(56) References Cited

U.S. PATENT DOCUMENTS

| 4,969,909 | A | * | 11/1990 | Barouk | A61B 17/72 |
| | | | | | 606/62 |
| 5,938,623 | A | | 8/1999 | Quiachon | |
| 6,425,887 | B1 | | 7/2002 | McGuckin | |
| 6,592,559 | B1 | | 7/2003 | Pakter | |
| 6,923,829 | B2 | * | 8/2005 | Boyle | A61F 2/89 |
| | | | | | 623/1.18 |
| 6,966,774 | B2 | * | 11/2005 | Brock | A61C 5/42 |
| | | | | | 433/102 |
| 7,632,303 | B1 | | 12/2009 | Stalker | |
| 7,837,466 | B2 | * | 11/2010 | Griffith | A61C 7/14 |
| | | | | | 433/17 |
| 8,048,030 | B2 | | 1/2011 | McGuckin | |
| 8,052,661 | B2 | | 11/2011 | McGuckin | |
| 8,287,541 | B2 | | 10/2012 | Nelson | |
| 8,361,102 | B2 | | 1/2013 | Geist | |
| 8,361,131 | B2 | | 1/2013 | Chin | |

(Continued)

*Primary Examiner* — Kevin T Truong
*Assistant Examiner* — Tracy L Kamikawa
(74) *Attorney, Agent, or Firm* — McDonnell Boehnen Hulbert & Berghoff LLP

(57) ABSTRACT

The present disclosure provides an apparatus comprising a wire having a first end and a second end opposite the first end. A first portion of the wire including the first end comprises a malleable region that is configured to remain deformed after bending, and a second portion of the wire including the second end comprises a superelastic region that is configured to return to a straight configuration after bending.

20 Claims, 5 Drawing Sheets

(56) References Cited

U.S. PATENT DOCUMENTS

| | | |
|---|---|---|
| 8,439,916 B2 | 5/2013 | Coati |
| 8,540,676 B2 | 9/2013 | Geist |
| 8,540,747 B2 | 9/2013 | Geist |
| 8,545,531 B2 | 10/2013 | Geist |
| 8,597,337 B2 | 12/2013 | Champagne |
| 8,668,668 B2 * | 3/2014 | Bishop .............. A61M 25/0662 |
| | | 604/103.06 |
| 8,715,311 B2 | 5/2014 | Geist |
| 8,728,111 B2 | 5/2014 | Geist |
| 8,747,359 B2 | 6/2014 | Pakter |
| 8,758,268 B2 | 6/2014 | Bown |
| 8,784,382 B2 | 7/2014 | McGuckin |
| 8,864,804 B2 | 10/2014 | Champagne |
| 8,915,916 B2 | 12/2014 | Duncan |
| 8,974,485 B2 | 3/2015 | Geist |
| 8,979,889 B2 | 3/2015 | Geist |
| 9,474,561 B2 | 10/2016 | Shemwell |
| 9,545,274 B2 | 1/2017 | McCormick |
| 9,675,392 B2 | 6/2017 | Shemwell |
| 9,802,024 B2 | 10/2017 | McGuckin |
| 9,855,036 B2 | 1/2018 | Palmer |
| 2007/0154859 A1 * | 7/2007 | Hilliard ................. A61C 7/20 |
| | | 433/20 |
| 2011/0313453 A1 * | 12/2011 | Krumme ........... A61B 17/0401 |
| | | 606/232 |
| 2013/0017506 A1 * | 1/2013 | Parker .................. A61C 7/28 |
| | | 433/24 |
| 2014/0094778 A1 * | 4/2014 | Bown .................. A61M 25/09 |
| | | 604/510 |
| 2014/0303600 A1 | 10/2014 | Bown |
| 2015/0133940 A1 * | 5/2015 | Palmer ............... A61B 17/068 |
| | | 606/75 |
| 2017/0296798 A1 * | 10/2017 | Kume ............... A61M 25/0068 |
| 2018/0021107 A1 * | 1/2018 | Benarouch .............. A61C 7/14 |
| | | 433/6 |
| 2020/0197669 A1 * | 6/2020 | Grummon ............. A61L 31/14 |

* cited by examiner

VARIABLE STIFFNESS HAMMERTOE K-WIRE AND METHODS FOR USE

RELATED APPLICATIONS

This application claims the benefit of priority to U.S. Provisional Application No. 62/754,023 entitled "Variable Stiffness Hammertoe K-Wire and Methods for Use," filed on Nov. 1, 2018, the contents of which are hereby incorporated by reference in their entirety.

BACKGROUND

Correction of hammertoe deformities using Kirschner wires ("K-wires") can fail due to post-surgery movement of the foot/phalanges. In cases of extreme post-surgical movement, the K-wires can plastically deform; i.e., the K-wire can take a permanent set and remain deformed, or break. A deformed K-wire can negatively affect fusion at the joint site and make removal of the K-wire more difficult for the surgeon at the 3-6 week post-operative mark. Other issues with K-wires include, but not limited to, bulky diameters requiring removal of a substantial amount of bone, incompatibility with hammertoe implants, and incompatible modulus of the alloy, which can be substantially higher relative to the modulus of bone. Therefore, methods and devices are disclosed herein that address these issues.

SUMMARY

Shape memory K-wires and methods of use are disclosed that address challenges of existing hammertoe devices and procedures. K-wires having malleable and superelastic regions and a modulus closer to that of bone are disclosed. Use of a shape memory metal, such as superelastic Nitinol, allows a K-wire to take extreme positions without plastic deformation. For example, a straight superelastic Nitinol wire can take a bend of at least 90° and return to its original, straight position. A comparable stainless steel K-wire is unable to bend to such an angle and return to a straight position. The ability of a K-wire to return to its original, straight, position eliminates issues associated with metal deformation for non-conforming patients during their recovery period. A shape memory hammertoe K-wire is processed so that the distal end of the K-wire is malleable. This malleable region allows the surgeon to easily cut and crimp this distal end of the K-wire as they would normally do with a stainless steel K-wire.

Thus, in a first aspect, an apparatus is provided comprising a wire having a first end and a second end opposite the first end, wherein a first portion of the wire including the first end comprises a malleable region that is configured to remain deformed after bending, and wherein a second portion of the wire including the second end comprises a superelastic region that is configured to return to a straight configuration after bending.

In a second aspect, an apparatus is provided comprising (a) a wire having a first end and a second end opposite the first end, wherein a first portion of the wire including the first end comprises a shape set superelastic region, and wherein a second portion of the wire including the second end comprises a straight superelastic region that is configured to return to a straight configuration after bending, and (b) a sleeve including a lumen, wherein the first portion of the wire is removably positioned at least partially in the lumen of the sleeve, wherein the first portion of the wire is in a constrained state when the first portion of the wire is positioned at least partially in the lumen of the sleeve, wherein the first portion of the wire is substantially straight in the constrained state, wherein the first portion of the wire is in an unconstrained state when the first portion of the wire is removed from the lumen of the sleeve, and wherein the first portion of the wire has a non-zero angle with respect to the second portion of the wire in the unconstrained state.

In a third aspect, a method is provided comprising (a) introducing a second end of a wire into a joint, wherein a superelastic portion of the wire including the second end is configured to return to a straight configuration after bending to thereby maintain the joint in a straightened position, and (b) cutting a first end of the wire.

In a fourth aspect, a method is provided comprising (a) introducing a second end of a wire into a joint, wherein a straight superelastic region including the second end of the wire is configured to return to a straight configuration after bending to thereby maintain the joint in a straightened position, and (b) removing a first end of the wire from a lumen of a sleeve to transition the wire from a constrained state to an unconstrained state, wherein the first end of the wire has a non-zero angle with respect the second end of the wire in the unconstrained state.

These as well as other aspects, advantages, and alternatives, will become apparent to those of ordinary skill in the art by reading the following detailed description, with reference where appropriate to the accompanying drawings.

DETAILED DESCRIPTION

Shape memory K-wires and methods of use are disclosed that address challenges of existing hammertoe devices and procedures. A shape memory K-wire can comprise a malleable distal end, while the remaining portion of the K-wire is superelastic at room temperature. In use, a surgeon can use a nitinol K-wire to stabilize an osteotomy site. A proximal superelastic region will spring back to its original position after being bent while positioned in a joint of a patient, while the malleable region allows a surgeon to easily cut and crimp this distal end of the K-wire. The shape memory K-wire can be left in the bone for 3 to 6 weeks while the osteotomy heals. Post-surgery (e.g., 3 to 6 weeks), a surgeon can retract the nitinol K-wire out of the distal end of the toe, leaving no metal hardware behind in the patient. In another embodiment, a shape memory K-wire can be used during a procedure to guide a cannulated hammertoe implant into a joint. An implant is intended to stay in the patient in perpetuity, while the shape memory K-wire is either withdrawn during the procedure or retracted from the patient at a later time.

Figure 1:
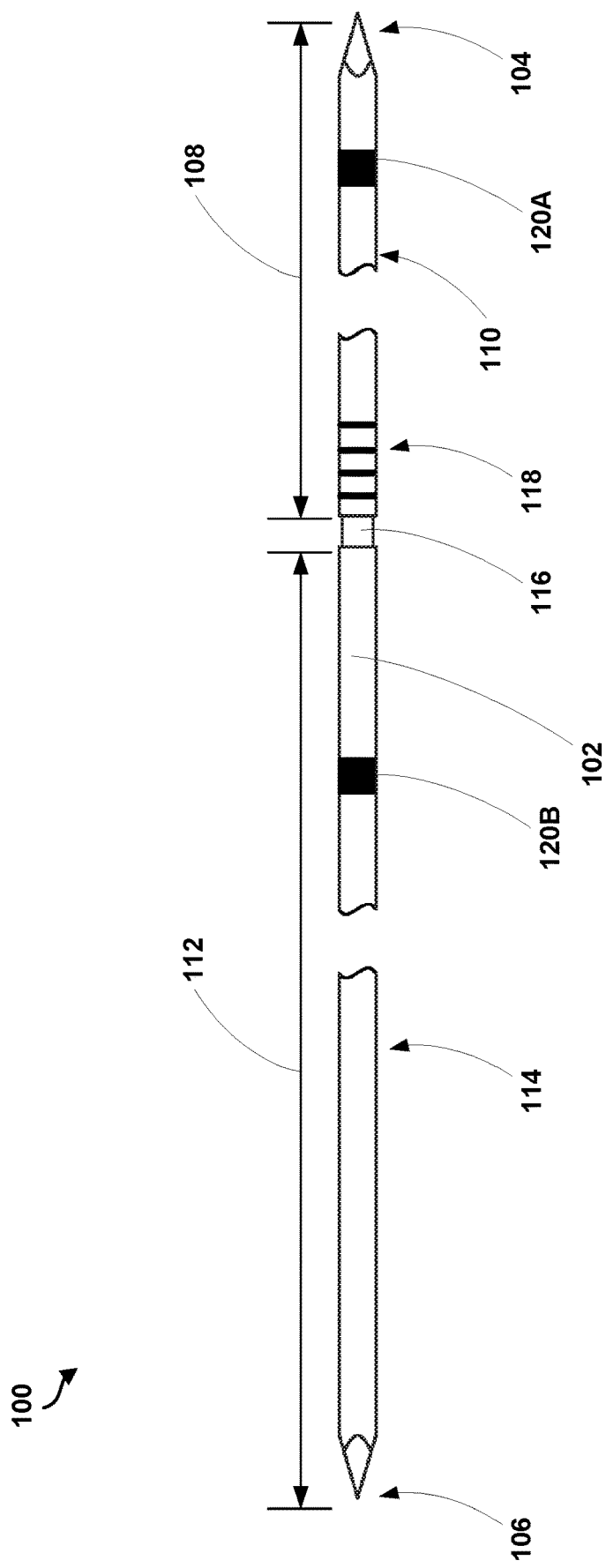
FIG. 1 illustrates an apparatus, according to an example embodiment.

FIG. 1 illustrates an apparatus 100 comprising a wire 102 having a first end 104 and a second end 106 opposite the first end 104. A first portion 108 of the wire 102 including the first end 104 comprises a malleable region 110 that is configured to remain deformed after bending. In one example, the malleable region 110 comprises the entirety of the first portion 108 of the wire 102. In another example, the malleable region 110 comprises a subset of the first portion 108 of the wire 102. A modulus of elasticity of the malleable region 110 of the wire 102 may be about 28 GPa to about 40 GPa (e.g., about 28, 30, 32, 33, 34, 36, 38, or 40 GPa).

A second portion 112 of the wire 102 including the second end 106 comprises a superelastic region 114 that is configured to return to a straight configuration after bending. As such, the second portion 112 may comprise an austenitic region of the wire 102. The superelastic region 114 of the wire is superelastic at room temperature. In one example, the superelastic region 114 comprises the entirety of the second portion 112 of the wire 102. In another example, the superelastic region 114 comprises a subset of the second portion 112 of the wire 102. A modulus of elasticity of the superelastic region 114 may be about 40 GPa to about 80 GPa (e.g., about 40, 45, 50, 55, 60, 65, 70, 75, or 80 GPa).

Figure 2:
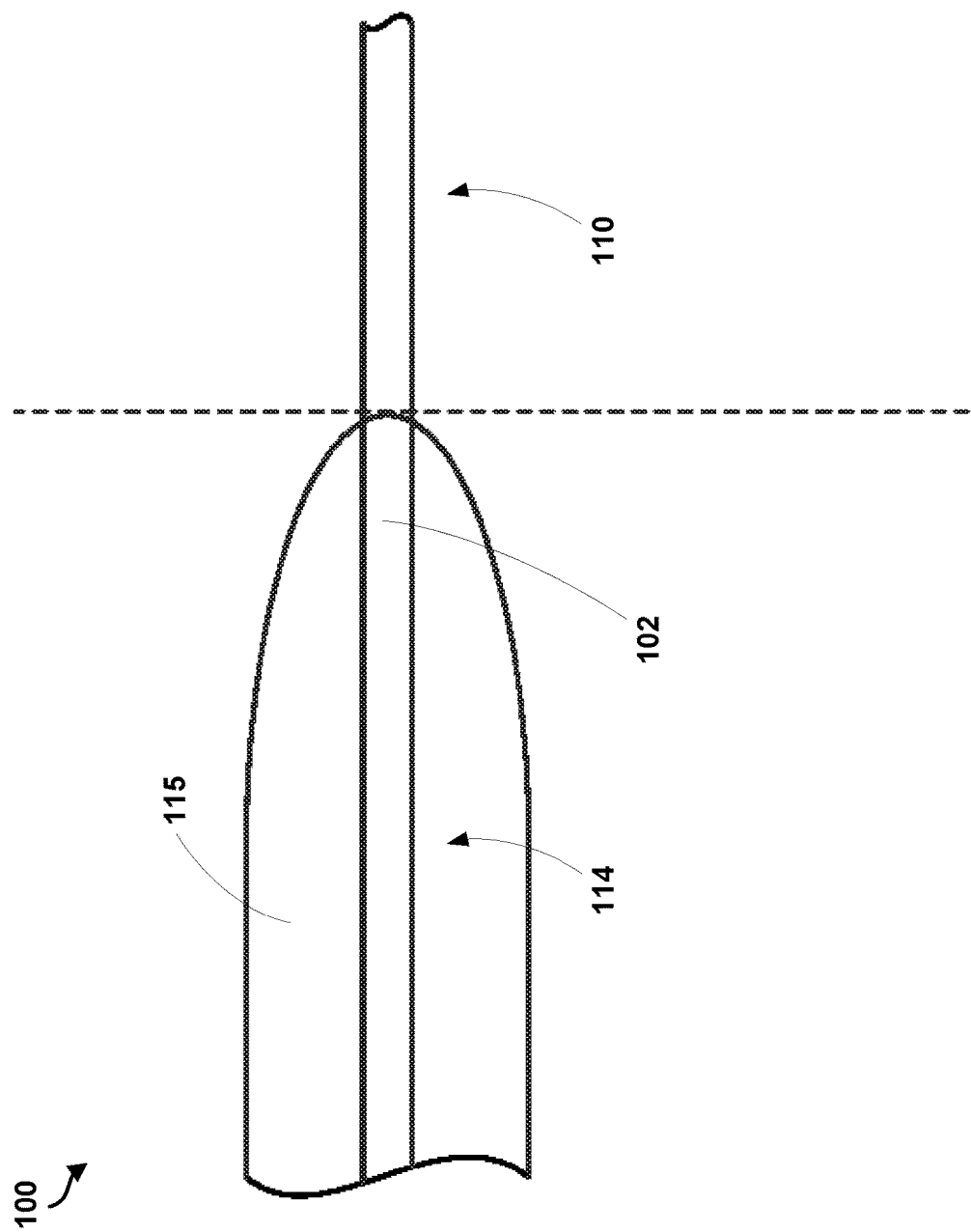
FIG. 2 illustrates the apparatus of FIG. 1 positioned in a digit of a patient, according to an example embodiment.

In use, as shown in FIG. 2 and as discussed in additional detail below, any of the disclosed embodiments can be used in a hammertoe procedure and can be positioned in a digit 115 of a patient, more particularly across a joint of a toe of the patient. In an example, a second portion 112, which includes a superelastic region 114 including a second end 106, is positioned in the digit 115 of the patient and a first portion 108, which includes a malleable region 110 including a first end 104, extends out of the digit 115 of the patient. In an embodiment, the apparatus 100 can then be left in the patient post-surgery (e.g., 3-6 weeks) to provide temporary support while the joint is healing.

Figure 3:
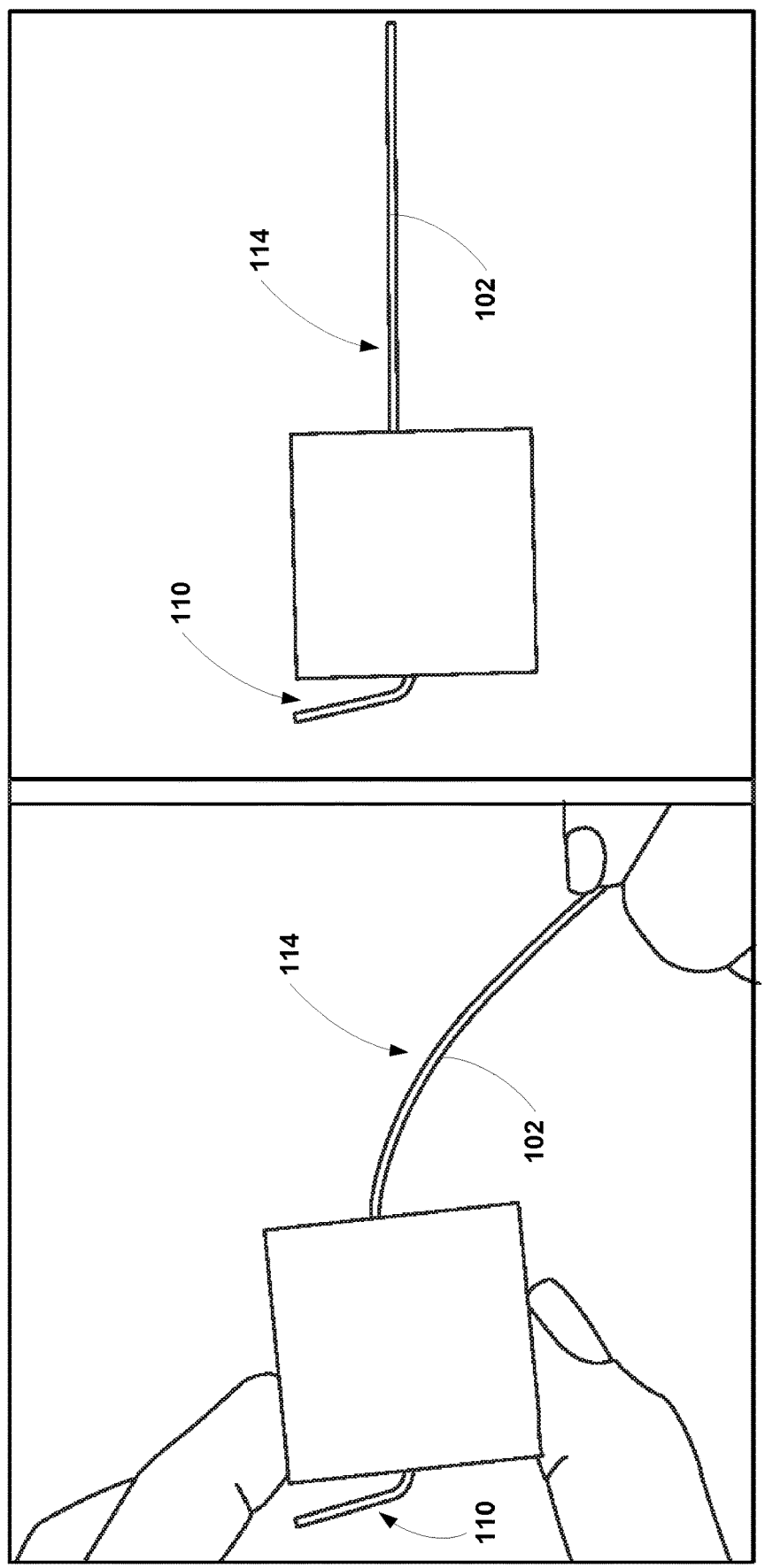
FIG. 3 illustrates the apparatus of FIG. 1 with the first portion bent and returning to a straight configuration, according to an example embodiment.

A superelastic region 114 of a wire 102 allows a second portion 112 of the wire 102 positioned in the patient to bend in response to movement of the patient post-surgery, but will snap back to its straight configuration due to its superelastic properties as illustrated in FIG. 3. Such a configuration prevents permanent deformation of a second portion 112 of a wire 102 that is positioned in the patient, which can negatively affect the healing process of a joint. In addition, such a configuration keeps a second portion 112 of a wire 102 substantially straight, which makes removal of the apparatus from the patient easier. A malleable region 110 of the wire 102 allows a surgeon to cut and optionally crimp a first end 104 of the wire 102 to thereby prevent the wire 102 from sliding along the joint after the procedure. In another example, the surgeon may cut off a portion of the malleable region 110 of the wire 102 and leave the remaining malleable region 110 of the wire 102 substantially straight.

A wire 102 may comprise a shape memory alloy. The shape memory alloy may comprise a Ni—Ti alloy, or a Cu—Al—Ni—Mn alloy, as non-limiting examples. In one particular example, the wire 102 comprises Nitinol, which is a Ni—Ti alloy. A number of different Nitinol raw materials can be used for a wire 102 in order to optimize and achieve the desired characteristics (e.g., strength, transition temperature) of the wire 102. A wire 102 can comprise Nitinol of varied ultimate tensile strengths, % elongation, loading and unloading plateaus, and austenite finishing temperatures.

In addition, Nitinol has a modulus of elasticity (~40 GPa to 80 GPa) more comparable to bone (~15 GPa) than stainless steel (~200 GPa). Moreover, Nitinol's hysteresis (stress/strain curve) is more similar to human tissue than stainless steel. Superelastic Nitinol will allow the phalanges to flex in a more physiologically naturally manner than the stiffer stainless steel. Therefore, use of a Nitinol wire for a hammertoe procedure limits the potential for stress shielding and can result in better rates of proximal interphalangeal fusion healing.

A length of the first portion 108 of the wire 102 can be less than a length of the second portion 112 of the wire 102. In one particular example, a ratio of the length of the first portion 108 of the wire 102 to the length of the second portion 112 of the wire 102 can be about 6:1 to about 1:6, for example from about 3:1 to about 1:3. The length of the first portion 108 of the wire 102 can be about 10 mm to about 600 mm, and the length of the second portion 112 of the wire 102 can be about 10 mm to about 300 mm.

Figure 4:
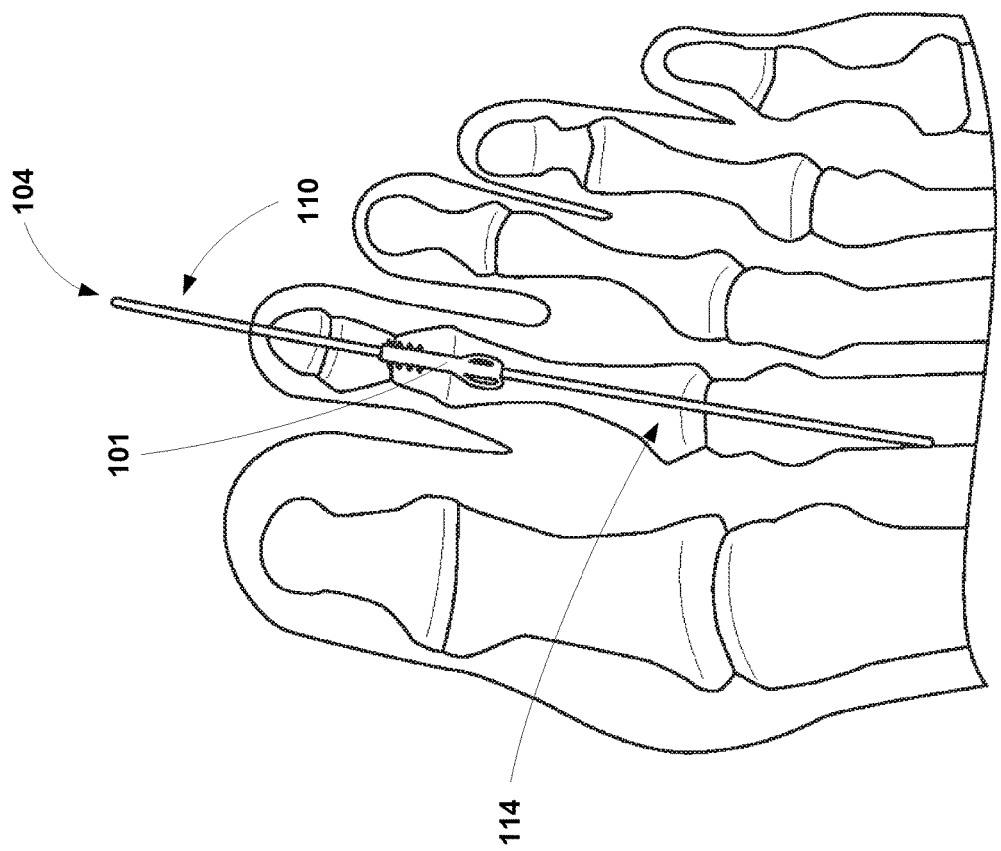
FIG. 4 illustrates the apparatus of FIG. 1 positioned in a joint of a patient with a hammertoe implant positioned on the apparatus, according to an example embodiment.

A diameter of the wire 102 can be about 0.7 mm to about 4.0 mm (e.g., about 0.7, 0.8, 0.9, 1.0, 1.1, 1.5, 2.0, 2.5, 3.0, 3.5, or 4.0 mm). The superelastic characteristics of the wire 102 can result in better fatigue resistance than a traditional stainless steel K-wire of the same size. Better resistance to fatigue, in turn, equates to less susceptibility to plastic deformation. Therefore, it is possible to achieve better resistance to plastic deformation with a smaller (e.g., 1.1 mm) wire than with a larger (1.6 mm) stainless steel K-wire. A smaller shape memory alloy K-wire diameter can result in bone preservation at the surgical site. In addition, a smaller diameter wire can increase the ability for the wire 102 to receive various hammertoe implants. For example, the wire 102 can have a 1.1 mm diameter, and therefore can be able to accept a hammertoe implant 101 such as a DynaNite® Hammertoe Implant (FIG. 4). In an example, a diameter of the first portion 108 of the wire 102 is the same as a diameter of the second portion 112 of the wire 102. In another example, a diameter of the first portion 108 of the wire 102 is different than a diameter of the second portion 112 of the wire 102.

A malleable region 110 of a wire 102 can be created through a variety of processes. In an example, a malleable region 110 of a wire 102 is created through differential heat treatment during the manufacturing process. In one particular example, a differential heat treatment process comprises heating a first portion 108 of a wire 102 very quickly to red-hot and then rapidly cooling (e.g., quenching), turning only the first portion 108 into a malleable form but leaving a second portion 112 of the wire 102 in its unchanged superelastic form. In another example, a malleable region 110 of a wire 102 is created through ablation of the nickel content of a first portion 108 of the wire 012. For example, an approximate 0.1% decrease in Nitinol's nickel alloy composition can equate to a change between about 20° C. to about 40° C. in austenitic finish transformation temperature. In one particular example, about 0.05% of the nickel from a first end 104 of a wire 102 can be ablated away, which will correspondingly increase the martensitic start and austenitic finish temperatures a malleable region 110 of the wire 102. Such an ablation method is a precise method of controlling the length of a malleable region 110 of a wire 102. A transition region between a malleable region 110 and a superelastic region 114 of the wire 102 can be non-existent (i.e., the malleable region 110 transitions to the superelastic region 114 without any region between them that exhibit blended properties) or the transition region between the malleable region 110 and the superelastic region 114 can be as long as the malleable region 110 itself, and exhibit properties of both regions.

In another example, a malleable region 110 of a wire 102 is created by processing the first portion 108 in a fully annealed condition, such that it will be completely malleable and have no superelastic or shape memory response with any temperature change. Annealing is a process of removing all residual stresses that were a result of cold work during the manufacturing process using high heat. Such an annealing process removes all superelasticity and shape memory properties of cold-worked Nitinol. In another example, partial annealing can be performed at a lower temperature and for specified amounts of time and will remove some, but not all of the residual stress and thus results in an increase in $A_f$ and altering of the original tensile properties.

In an example, a first portion 108 of the wire 102 can have an austenitic start temperature greater than 22° C. (e.g., 22, 23, 24, 25, 26, 27, 28, 29, 30° C. or more). Thereby, a first portion 108 can be malleable when positioned outside of the body in ambient air. Then a second portion 112 of a wire 102 can have an austenitic finish temperature less than 37° C. (e.g. 37, 36, 35, 34, 33, 32, 31° C., or less). In particular, the austenitic finish temperature of a second portion 112 of a wire 102 can be about −5° C. to about 26° C. (e.g., about −5, −4, −3, −2, −1, 0, 1, 2, 3, 4, 5, 6, 7, 8, 9, 10, 11, 12, 13, 14, 15, 16, 17, 18, 19, 20, 21, 22, 23, 24, 25, or 26° C.). Thus, a second portion 112 can be superelastic when positioned in the body. A loading plateau of a first portion 108 of a wire 102 can be less than about 45 ksi (e.g., 45, 44, 43, 42, 41, 40, 35, 30 ksi or less), and a loading plateau of a second portion 112 of a wire 102 can be about 55 ksi to about 80 ksi (e.g., about 55, 60, 65, 70, 75, or 80 ksi).

In an example, as shown in FIG. 1, an apparatus 100 can also include a transition zone marker 116 positioned on a transition region of the wire 102 between a first portion 108 and a second portion 112 of the wire 102. The transition zone marker 116 can comprise a brightly colored band that provides a visual indication for the surgeon on where the superelastic region 114 transitions to the malleable region 110, thereby enabling the surgeon to know where to cut and optionally crimp the malleable region 110 after positioning the superelastic region 114 of the wire 102 in the patient. In another example, a first portion 108 of a wire 102 includes one or more measurement markings 118 indicating a length of the first portion 108. Such an arrangement may provide an indication of the depth of the wire 102 in the patient.

In another example, a first portion 108 of a wire 102 and/or a second portion 112 of a wire 102 includes a marker 120A, 120B. Such a marker may take a variety of forms, including a radio-opaque marker, a laser marking, or a color coating, as non-limiting examples. In one particular example, an entirety of the malleable region 110 may be coated a different color than the rest of the wire 102. In another particular example, a first portion 108 of a wire 102 includes a first a radio-opaque marker 120A visible under fluoroscopy, and a second portion 112 of the wire 102 includes a second a radio-opaque marker 120B visible under fluoroscopy (for example, Platinum or Tantalum). Such a configuration enables the surgeon to view the respective regions of the apparatus 100 as they are positioned in the patient. In one example, the first radio-opaque marker 120A is the same as the second radio-opaque marker 120B. In another example, a first radio-opaque marker 120A is different than a second radio-opaque marker 120B. In another example, only a first portion 108 of a wire 102 includes a radio-opaque marker 120A. In another example, only the second portion 112 of a wire 102 includes a radio-opaque marker 120B.

A first end 104 and/or a second end 106 of the wire 102 can comprise a sharp tapered end to help with positioning the apparatus 100 across a joint of the patient, as shown in FIG. 1. In one particular example, the first end 104 and/or the second end 106 of the wire can be pyramidal in shape, providing three or more cutting edges where each face joins and adjacent face. In another example, the first end 104 and/or the second end 106 of the wire 102 can be threaded to enable attachment of additional components having complementary threads. In another example, the first end 104 and/or the second end 106 of the wire 102 can be blunt.

Figure 5A:
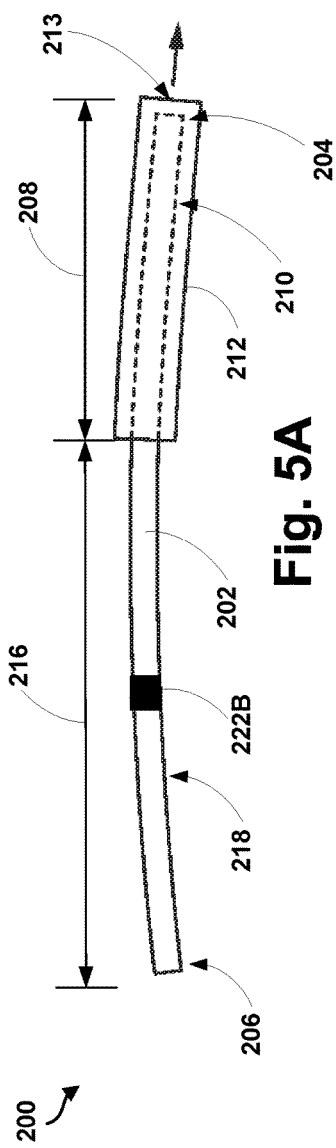
FIG. 5A illustrates another apparatus in a constrained state, according to an example embodiment.
Figure 5B:
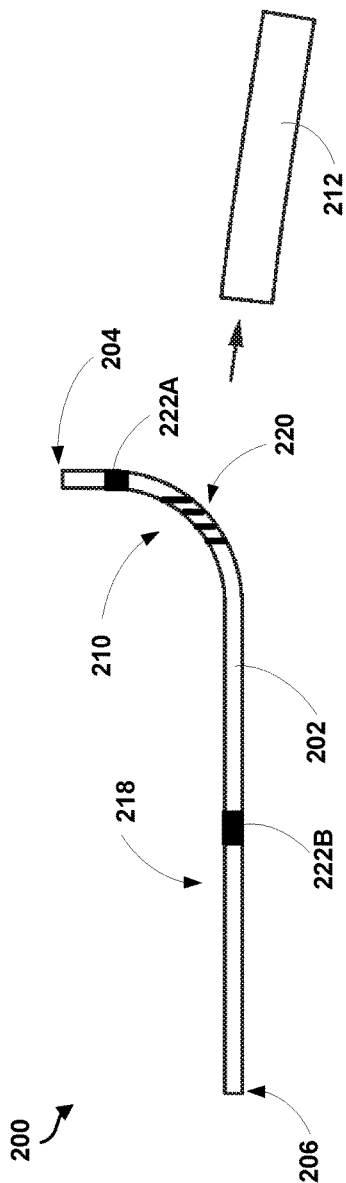
FIG. 5B illustrates the apparatus of FIG. 5A in an unconstrained state, according to an example embodiment.
Figure 5C:
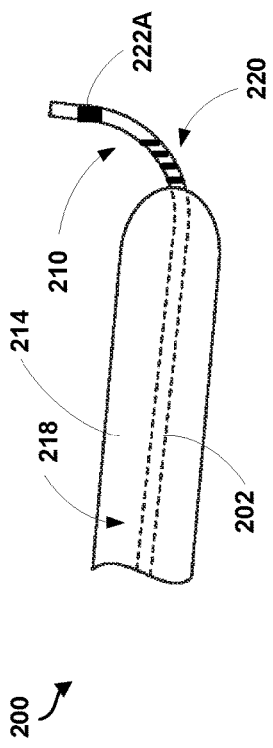
FIG. 5C illustrates the apparatus of FIG. 5A positioned in a digit of a patient, according to an example embodiment.

FIGS. 5A-5C illustrates another embodiment of an apparatus 200. In FIG. 5A, the apparatus 200 comprises a wire 202 having a first end 204 and a second end 206 opposite the first end 204. A first portion 208 of the wire 202 including the first end 204 comprises a shape set superelastic region 210. In an example, the wire 202 can be manufactured entirely of superelastic nitinol, and can have a first end 204 that is shape set in a bent configuration. The shape set superelastic region 210 is then straightened in a constrained condition when a sleeve 212 is positioned over the first end 204 of the wire 202, as shown in FIG. 5A. Once the constraint of the sleeve 212 is removed as illustrated in FIG. 5B, the shape set bent shape can be recovered. This as-manufactured shape of a first portion 208 of a wire 202 will specifically conform to the desired post-surgical shape. Namely, a first end 204 of the wire 202 can be bent upwards at the point that will extrude beyond the tip of the digit 214. As such, the shape set superelastic region 210 of the wire 202 has a non-zero angle with respect to a second portion 216 of the wire 202 when a first portion 208 of the wire 202 is in an unconstrained state. FIG. 5C illustrates a wire 202 in an unconstrained state after the wire 202 has been positioned in a digit 214 of a patient.

A second portion 216 of the wire 202 including the second end 206 comprises a straight superelastic region 218 that is configured to return to a straight configuration after bending. Such a configuration prevents permanent deformation of the wire 202 in a patient, which can negatively affect the healing process of the joint as discussed above. In addition, such a configuration keeps a second portion 216 of a wire 202 substantially straight, which makes removal of the apparatus 200 from the patient easier.

An apparatus 200 as disclosed herein can also include a sleeve 212 having a lumen 213. The sleeve 212 can be made from aluminum, steel, or titanium as non-limiting examples. A first portion 208 of a wire 202 can be removably positioned at least partially in the lumen 213 of the sleeve 212. A first portion 208 of a wire 202 is in a constrained state when the first portion 208 of the wire 202 is positioned at least partially in the lumen 213 of the sleeve 212. A first portion 208 of a wire 202 can be substantially straight in the constrained state. In particular, a longitudinal axis of a first portion 208 of a wire 202 can be coaxial with a longitudinal axis of a second portion 216 of the wire 202 when the first portion 208 of the wire 202 is in the constrained state, as shown in FIG. 5A. A first portion 208 of a wire 202 can be in an unconstrained state when the first portion 208 of the wire 202 is removed from a lumen 213 of a sleeve 212. A first portion 208 of a wire 202 can have a non-zero angle with respect to a second portion 216 of a wire 202 in the unconstrained state, as shown in FIG. 5B. In particular, a longitudinal axis of a first portion 208 of a wire 202 can have a non-zero angle with respect to a longitudinal axis of a second portion 028 of a wire 202 when the first portion 208 of the wire 202 is in the unconstrained state.

In an example, a diameter of a lumen 213 of a sleeve 212 is adjustable. As such, the sleeve 212 can transition from a first diameter where the lumen 213 of the sleeve 212 contacts a wire 202 to hold a first portion 208 of the wire 202 in the constrained state, to a second larger diameter that enables the first portion 208 of the wire 202 to be removed from the lumen 213 of the sleeve 212 to transition the first portion 208 of the wire 202 to the unconstrained state.

The wire 202 of the apparatus 200 of, for example, FIGS. 5A-5C can be similarly configured to the wire 102 of the apparatus 100 of, for example, FIG. 1. In particular, a length of a first portion 208 of a wire 202 can be less than a length of a second portion 216 of the wire 202. In one particular example, a ratio of the length of a first portion 208 of a wire 202 to the length of a second portion 216 of the wire 202 can be about 6:1 to about 1:6, for example from about 3:1 to about 1:3. The length of a first portion 208 of a wire 202 can be about 10 mm to about 100 mm, and the length of a second portion 216 of the wire 202 can be about 10 mm to about 100 mm.

A diameter of a wire 202 can be about 0.7 mm to about 4 mm (e.g., about 0.7, 0.8, 0.9, 1.0, 1.1, 1.5, 2.0, 2.5, 3.0, 3.5, or 4.0 mm). In an example, a diameter of a first portion 208 of a wire 202 is the same as a diameter of a second portion 216 of the wire 202. In another example, a diameter of a first portion 208 of a wire 202 is different than a diameter of a second portion 216 of the wire 202.

In an example, a first portion 208 of a wire 202 includes one or more measurement markings 220 indicating a length of the first portion 208 of the wire 202. Such an arrangement may provide an indication of the depth of the wire 202 in the patient. In another example, a first portion 208 of a wire 202 and/or a second portion 216 of a wire 202 includes a marker 222A, 222B. Such a marker may take a variety of forms, including a radio-opaque marker, a laser marking, or a color coating, as non-limiting examples. In one particular example, an entirety of a first portion 208 of a wire may be coated a different color than the rest of the wire 202. In another particular example, a first portion 208 of a wire 202 includes a first a radio-opaque marker 222A visible under fluoroscopy, and a second portion 216 of the wire 202 includes a second a radio-opaque marker 222B visible under fluoroscopy (for example, Platinum or Tantalum). Such a configuration enables the surgeon to view the respective regions of the apparatus 200 as they are positioned in the patient. In one example, the first radio-opaque marker 222A is the same as the second radio-opaque marker 222B. In another example, a first radio-opaque marker 222A is different than a second radio-opaque marker 222B. In another example, only a first portion 208 of a wire 202 includes a radio-opaque marker 222A. In another example, only a second portion 216 of a wire 202 includes a radio-opaque marker 222B.

A first end 204 and/or a second end 206 of a wire 202 can comprise a sharp tapered end to help with positioning the apparatus across a joint of the patient. In one particular example, a first end 204 and/or a second end 206 of a wire 202 can be pyramidal in shape, providing three or more cutting edges where each face joins and adjacent face. In another example, a first end 204 and/or a second end 206 of a wire 202 can be threaded to enable attachment of additional components having complementary threads. In another example, a first end 204 and/or a second end 206 of a wire 202 can be blunt.

In operation, an example method can include (a) introducing a second end 106 of a wire 102 into a joint, wherein a superelastic portion 114 of the wire 102 including the second end 106 is configured to return to a straight configuration after bending to thereby maintain the joint in a straightened position, and (b) cutting a first end 104 of the wire 102. A wire 102 can be introduced following removal of one or more portions of a joint in a toe of a patient. The methods can result in straightening the joint.

In one example, the first end 104 of the wire is superelastic such that the entirety of the wire 102 is superelastic. In another example, the first end 104 of the wire is malleable. In such an example, an embodiment of the methods can further include bending the malleable first end 110 of the wire 102 to permanently deform the first end 104 such that the malleable first end 110 of the wire 102 has a non-zero angle with respect to the superelastic second end 114 of the wire 102. The methods can further include positioning a second end 106 of a wire 102 through a lumen in a hammertoe implant 101, and positioning the hammertoe implant 101 in a joint prior to cutting a first end 104 of the wire 102. The methods can further include removing the wire 102 from the joint. In one particular example, the wire 102 is removed from the joint after 3-6 weeks.

In one example, when the apparatus 100 is positioned in the patient, the entire malleable region 110 of the first portion 108 of the wire 102 is outside of the body of the patient. In another example, when the apparatus 100 is positioned in the patient, a portion of the malleable region 110 of the first portion 108 of the wire 102 remains inside of the body of the patient. In yet another example, when the apparatus 100 is positioned in the patient, the entire malleable region 110 of the first portion 108 of the wire 102 is positioned distal to a distalmost joint of the patient though which the wire 102 is positioned.

Another example method can include (a) introducing a second end 206 of a wire 202 into a joint, wherein a straight superelastic region 218 including the second end 206 of the wire 202 is configured to return to a straight configuration after bending to thereby maintain the joint in a straightened position, and (b) removing a first end 204 of the wire 202 from a lumen 213 of a sleeve 212 to transition the wire 202 from a constrained state to an unconstrained state, wherein the first end 204 of the wire 202 has a non-zero angle with respect the second end 206 of the wire 202 in the unconstrained state. A wire 202 also can be introduced following removal of one or more portions of a joint in a toe of a patient. The methods can result in straightening the joint.

The methods can further include positioning a second end 206 of a wire 202 through a lumen in a hammertoe implant 101, and positioning the hammertoe implant 101 in a joint. The method can also include removing the wire 202 from the joint. In one particular example, the wire 202 is removed from the joint after 3-6 weeks.

In one example, when the apparatus 200 is positioned in the patient, the entire shape set superelastic region 210 of the first portion 208 of the wire 202 is outside of the body of the patient. In another example, when the apparatus 200 is positioned in the patient, a portion of the shape set superelastic region 210 of the first portion 208 of the wire 202 remains inside of the body of the patient. In yet another example, when the apparatus 200 is positioned in the patient, the entire shape set superelastic region 210 of the first portion 208 of the wire 202 is positioned distal to a distalmost joint of the patient though which the wire 202 is positioned.

As used herein, with respect to measurements, "about" means+/−10%.

As used herein, "substantially straight" means a structure having a radius of curvature less than 5°.

Unless otherwise indicated, the terms "first," "second," etc. are used herein merely as labels, and are not intended to impose ordinal, positional, or hierarchical requirements on the items to which these terms refer. Moreover, reference to, e.g., a "second" item does not require or preclude the existence of, e.g., a "first" or lower-numbered item, and/or, e.g., a "third" or higher-numbered item.

As used herein, apparatus, element and method "configured to" perform a specified function is indeed capable of performing the specified function without any alteration, rather than merely having potential to perform the specified function after further modification. In other words, the apparatus, element, and method "configured to" perform a specified function is specifically selected, created, implemented, utilized, programmed, and/or designed for the purpose of performing the specified function. As used herein, "configured to" refers to existing characteristics of an apparatus, element, and method which enable the apparatus, element, and method to perform the specified function without further modification. For purposes of this disclosure, an apparatus, element, and method described as being "configured to" perform a particular function can additionally or alternatively be described as being "adapted to" and/or as being "operative to" perform that function.

As used herein, "first end" refers to the end that will be a "distal end" relative to an operator of the apparatus.

As used herein, "second end" refers to the end that will be a "proximal end" relative to an operator of the apparatus.

As used herein, "lumen" refers to a passage within a structure having a diameter sized to receive a wire therethrough.

As used herein, "austenite start temperature" is the temperature at which the martensite to austenite transformation begins on heating of an alloy.

As used herein, "austenite finish temperature" is the temperature at which martensite to austenite transformation is completed on heating of an alloy.

As used herein, "constrained state" refers to when the apparatus is disposed in or partially with a sleeve and is substantially straight.

As used herein, "unconstrained state" refers to when the apparatus has been positioned in the patient and is unsheathed from a sleeve.

As used herein, "loading plateau" means a region after a first yield point, where several percent strain can be accumulated with only a small stress increase. The end of the loading plateau is reached at about 8% strain. After that, there is another linear increase of stress with strain. Unloading from the end of the plateau region, causes the stress to decrease rapidly until an unloading plateau is reached where several percent strain is recovered with a minimal decrease in stress.

As used herein, "shape set" means resetting a shape of the wire or base material to a new, desired shape, with the same mechanical properties. The wire or base material will return to the new, desired shape in the absence of outside forces acting on the wire or base material.

It will be appreciated that other arrangements are possible as well, including some arrangements that involve more or fewer steps than those described above, or steps in a different order than those described above.

While various aspects and embodiments have been disclosed herein, other aspects and embodiments will be apparent to those skilled in the art. All embodiments within and between different aspects of the devices and methods can be combined unless the context clearly dictates otherwise. The various aspects and embodiments disclosed herein are for purposes of illustration and are not intended to be limiting, with the true scope and spirit being indicated by the claims.

The invention claimed is:

1. An apparatus comprising:
a wire having a first portion including a first end and a second portion including a sharp tapered second end opposite the first end, wherein the first portion of the wire is configured to transition from a straight configuration along a longitudinal axis of the wire to a bent configuration in response to a bending applied to the first portion when positioned outside of a body of a patient in ambient air, wherein the first portion is configured to remain in the bent configuration after release of the bending, and wherein the second portion of the wire comprises a region that is superelastic in ambient air and is configured to return to the straight configuration a along the longitudinal axis of the wire after bending of the superelastic region when the second portion is positioned inside the body of the patient.

2. The apparatus of claim 1, wherein a length of the first portion of the wire is less than a length of the second portion of the wire.

3. The apparatus of claim 1, wherein a ratio of a length of the first portion of the wire to a length of the second portion of the wire is about 3:1 to about 1:3.

4. The apparatus of claim 1, wherein a length of the first portion of the wire ranges from about 10 mm to about 600 mm, and wherein a length of the second portion of the wire is about 10 mm to about 300 mm.

5. The apparatus of claim 1, wherein a diameter of the wire is about 0.6 mm to about 4 mm.

6. The apparatus of claim 1, wherein a diameter of the first portion of the wire is equal to a diameter of the second portion of the wire.

7. The apparatus of claim 1, wherein a diameter of the first portion of the wire is different than a diameter of the second portion of the wire.

8. The apparatus of claim 1, wherein the first portion of the wire has an austenitic start temperature greater than 22° C.

9. The apparatus of claim 1, wherein the second portion of the wire has an austenitic finish temperature less than 37° C.

10. The apparatus of claim 9, wherein the austenitic finish temperature of the second portion of the wire ranges from about −5° C. to about 26° C.

11. The apparatus of claim 1, wherein a loading plateau of the first portion of the wire is less than about 45 ksi, and wherein a loading plateau of the second portion of the wire ranges from about 55 ksi to about 80 ksi.

12. The apparatus of claim 1, further comprising a transition zone marker positioned on the wire between the first portion and the second portion.

13. The apparatus of claim 1, wherein the first portion and/or the second portion of the wire includes a marker.

14. The apparatus of claim 1, wherein the first portion of the wire includes one or more measurement markings indicating a length of the first portion.

15. The apparatus of claim 1, wherein the wire comprises a shape memory alloy.

16. A method comprising:
introducing the second end of the wire of claim 1 into a joint; and
cutting the first end of the wire.

17. The method of claim 16, wherein the first end of the wire is malleable.

18. The method of claim 17, further comprising:
bending the first portion of the wire to permanently deform the first portion such that the first end of the wire has a non-zero angle with respect to the second end of the wire.

19. The method of claim 16, further comprising:
positioning the second end of the wire through a lumen in a hammertoe implant; and
positioning the hammertoe implant in the joint prior to cutting the first end of the wire.

20. The method of claim 16, further comprising:
removing the wire from the joint.

\* \* \* \* \*